United States Patent [19]
Keihs et al.

[11] 3,960,885
[45] June 1, 1976

[54] SUCCINIC ACID OXIMIDOPHOSPHORIC ESTERS

[75] Inventors: Karl Keihs, Lampertheim; Heinrich Adolphi, Limburgerhof; Rolf Huber, Ludwigshafen, all of Germany

[73] Assignee: Badische Anilin- & Soda-Fabrik Aktiengesellschaft, Ludwigshafen (Rhine), Germany

[22] Filed: Nov. 14, 1974

[21] Appl. No.: 523,665

[30] Foreign Application Priority Data
Dec. 5, 1973 Germany............................ 2360493

[52] U.S. Cl............................ 260/326.5 A; 424/200
[51] Int. Cl.$^2$............................................ C07F 9/65
[58] Field of Search............................ 260/326.5 A

[56] References Cited
FOREIGN PATENTS OR APPLICATIONS
91,287    5/1959    Netherlands.................. 260/326.5 A OTHER PUBLICATIONS
Lorenz et al., C.A. 51, 15588a (1957).

*Primary Examiner*—Raymond L. Rush
*Assistant Examiner*—Mark L. Berch
*Attorney, Agent, or Firm*—Johnston, Keil, Thompson & Shurtleff

[57] ABSTRACT

New and valuable substituted succinic acid oximidophosphoric esters having a strong insecticidal action, pesticides containing these compounds as active ingredients, a process for controlling pests with these compounds, and a process for their production.

8 Claims, No Drawings

SUCCINIC ACID OXIMIDOPHOSPHORIC ESTERS

The present invention relates to new and valuable substituted succinic acid oximidophosphoric esters having a strong insecticidal action, pesticides containing these compounds as active ingredients, and a process for their production.

It is known (German 962,608) to use O,O-diethylsuccinic oximidothiophosphate for combatting insects. However, its action is poor.

We have now found that substituted succinic acid oximidophosphoric esters of the general formula

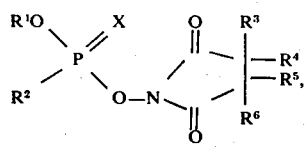

where X denotes sulfur or oxygen, $R^1$ denotes lower alkyl (methyl, ethyl, propyl), $R^2$ denotes lower alkoxy (methoxy, ethoxy), lower alkyl (methyl, ethyl), or aryl (phenyl), $R^3$ denotes alkyl ($C_1$ to $C_{10}$), cycloalkyl, alkenyl, cycloalkenyl, aryl (phenyl), or benzyl, $R^4$, $R^5$ and $R^6$ may be identical or different and each denotes hydrogen, lower alkyl ($C_1$ to $C_4$), or phenyl, or $R^3$ and $R^4$ together denote a hydrocarbon ring having several (five or six) members, have an excellent insecticidal action.

The new active ingredients may be prepared by reacting a phosphorylation agent of the formula

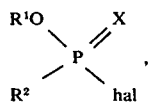

$R^1$, $R^2$ and X having the above meanings and hal denoting halogen (chloro, bromo), with a substituted succinic acid oximide of the formula

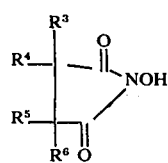

where $R^3$, $R^4$, $R^5$ and $R^6$ have the above meanings, in the form of its alkali metal salt or in the presence of an acid-binding agent.

The substituted succinic acid oximides, and their sodium salts, may be prepared by reaction of substituted succinic acid diesters with hydroxylamine alone, or if desired with the addition of suitable substances, e.g., sodium methylate, in accordance with the following scheme:

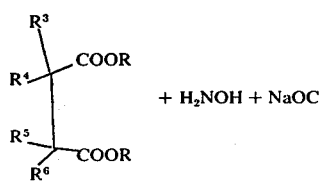

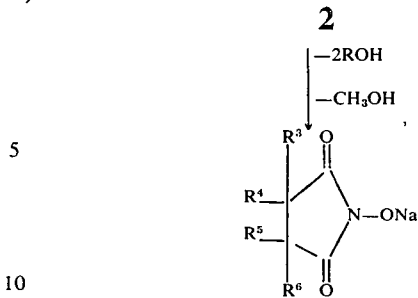

$R^3$, $R^4$, $R^5$ and $R^6$ having the above meanings, and R denoting lower alkyl. The substituted succinic acid oximides may be separated out by adding acid to the sodium salts. It is also possible to use appropriately substituted succinic anhydrides as starting materials, the procedure then being analogous to that described by G. Zinner in Arch. Pharm., 301, 776, 1968.

The substituted succinic acid diesters, succinic anhydrides and succinic acids required for the synthesis of the substituted succinic acid oximides are described in the literature.

The active ingredients are advantageously prepared in the presence of acid-binding agents. Suitable such agents are alkali metal carbonates, alcoholates and hydroxides, and organic bases, e.g., pyridine and trialkylamines. It is also possible to react the alkali metal salts of the abovementioned substituted succinic acid oximides with the abovementioned phosphoric halides. The reaction is advantageously carried out in an inert organic solvent at from 0° to 150°C, preferably 30° to 130°C. Particularly suitable solvents are ketones, benzene, toluene, xylene, dioxane, nitriles such as acetonitrile and propionitrile, dimethylformamide, dimethyl sulfoxide and esters of organic acids.

The phosphorylation components needed as starting materials are prior art.

The new phosphoric esters are either crystalline, or colorless to reddish oils which are sparingly soluble in water and are extremely difficult to distil, even at considerable subatmospheric pressure, without decomposition occuring. The compounds have an excellent action on a multiplicity of animal crop plant pests without damaging the plants themselves.

The new phosphoric esters are suitable for combatting for instance the following pests: in fruit:
Capua reticulana
Carpocapsa pomonella
Cheimatobia brumata
Psylla piri
Lyonetia clerkella
Nepticula malella
Adoxophyes orana
Rhagoletis cerasi
Aphis pomi
Hoplocampa brevis
in Indian corn:
Sesamia cretica
Chilo zonellus
Diatraea saccharalis
Prodenia ornitogalli
Laphygma frugiperda
in rice:
Nezara viridula
Chilo spec.
in groundnuts:
Aphis craccivora in sugar cane:
  *Odontotermes obesus*
in grapes:
  *Polychrosis botrana*
  *Sparganothis pilleriana*
in beet:
  *Aphis fabae*
  *Pegomya hyoscyami*
  *Cassida nobilis*
  *Agrotis segetum*
  *Piesma quadratum*
in cotton:
  *Heliothis zea*
  *Heliothis armigera*
  *Pectinophora gossypiella*
  *Dysdercus spec.*

Due to their excellent insecticidal properties the abovementioned products are most suitable for use as pesticides in the plant protection sector.

The insecticidal action may be broadened considerably by adding other insecticides, and adapted to existing conditions.

The preparation and use of the new compounds are illustrated by the following examples.

EXAMPLE 1

Solution of hydroxylamine in $CH_3OH$ 69 parts by weight of hydroxylamine hydrochloride is mixed with 100 parts of $CH_3OH$. While stirring and under nitrogen, 180 parts by weight of a 30 wt% technical grade solution of $NaOCH_3/CH_3OH$ is dripped in with external cooling. The mixture is finally stirred for 1 hour at 30°C. The sodium chloride is separated.

3,3-dimethylsuccinic acid oximide, sodium salt 174 parts by weight of 2,2-dimethylsuccinic acid dimethyl ester is dissolved in 100 parts of $CH_3OH$. The solution of hydroxylamine obtained above is added to this mixture while stirring. 180 parts by weight of a 30 wt% solution of $NaOCH_3/CH_3OH$ is subsequently dripped in over a period of 30 minutes. The mixture is then heated for 1 hour under reflux, after which time the reflux condenser is replaced by a short column and a descending condenser, and the methanol is distilled off, the portion which is removed being replaced by xylene (dripped in). The salt soon begins to precipitate colloidally. The internal temperature is finally raised to 135°C, pure xylene distilling off. The suspension of the sodium salt may subsequently be employed for phosphorylation, or the sodium salt is separated. There is obtained 165 parts by weight (100% of theory) of the sodium salt of 3,3-dimethylsuccinic acid oximide.

O,O-diethyl-O-(3,3-dimethylsuccinic acid oximido)-thionophosphate

The suspension of 165 parts by weight of the sodium salt of 3,3-dimethylsuccinic acid oximide in xylene obtained above is heated at 60°C; while stirring thoroughly, 188 parts by weight of diethoxythiophosphoryl chloride is dripped in. The mixture is stirred for 4 hours at this temperature and then allowed to cool. The precipitated sodium chloride is suction filtered, and the solution of the phosphoric ester in xylene is washed first with 200 parts by weight of a 10 wt% aqueous $NaHCO_3$ solution and then with 200 parts by weight of water, and is then dried over $Na_2SO_4$. After evaporation of the solvent a pale yellow oil remains.

Yield: 245 parts by weight = 83% of theory.

|  | C | H | N | P | S |
|---|---|---|---|---|---|
| Calcd.: | 40.7 | 6.1 | 4.7 | 10.5 | 10.8 |
| Found: | 41.0 | 6.7 | 4.3 | 10.2 | 10.6 |

$n_D^{25}$ : 1.4812.

The following compounds were prepared analogously:

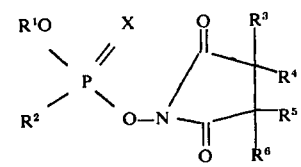

| No. | X | R$^1$ | R$^2$ | R$^3$ | R$^4$ | R$^5$ | R$^6$ | $n_D^{25}$ or m.p. |
|---|---|---|---|---|---|---|---|---|
| 3 | S | $CH_3$ | $CH_3O$ | $CH_3$ | $CH_3$ | H | H | 1.4832 |
| 4 | O | $CH_3$ | $CH_3O$ | $CH_3$ | $CH_3$ | H | H |  |
| 5 | S | $CH_3$ | $CH_3O$ | $CH_3$ | H | H | H | 1.4972 |
| 6 | S | $C_2H_5$ | $C_2H_5O$ | $CH_3$ | H | H | H | 1.4869 |
| 7 | S | $C_2H_5$ | $C_6H_5$ | $CH_3$ | $CH_3$ | H | H | 94 to 95°C |
| 8 | S | $C_2H_5$ | $C_6H_5$ | $CH_3$ | H | H | H | 1.5599 |
| 9 | S | $C_2H_5$ | $C_2H_5O$ | $CH_3$ | $CH_3$ | $CH_3$ | H |  |
| 10 | S | $C_2H_5$ | $C_2H_5O$ | $CH_3$ | $CH_3$ | $CH_3$ | $CH_3$ |  |
| 11 | S | $C_2H_5$ | $C_2H_5O$ | $C_2H_5$ | H | H | H |  |
| 12 | S | $C_2H_5$ | $C_2H_5O$ | $nC_3H_7$ | H | H | H |  |
| 13 | S | $C_2H_5$ | $C_2H_5O$ | $iC_3H_7$ | H | H | H |  |
| 14 | S | $C_2H_5$ | $C_2H_5O$ | $nC_4H_9$ | H | H | H |  |
| 15 | S | $C_2H_5$ | $C_2H_5O$ | $iC_4H_9$ | H | H | H |  |
| 16 | S | $C_2H_5$ | $C_2H_5O$ | $-CH_2-CH=CH_2$ | H | H | H |  |
| 17 | S | $C_2H_5$ | $C_2H_5O$ | $-CH\begin{smallmatrix}CH_3\\CH=CH_2\end{smallmatrix}$ | H | H | H |  |
| 18 | S | $C_2H_5$ | $C_2H_5O$ | (H) | H | H | H |  |
| 19 | S | $C_2H_5$ | $C_2H_5O$ | (phenyl) | H | H | H |  |
| 20 | S | $C_2H_5$ | $C_2H_5O$ | $C_6H_5$ | H | H | H | 1.4902 |
| 21 | S | $C_2H_5$ | $C_2H_5O$ | $CH_2-C_6H_5$ | H | H | H |  |

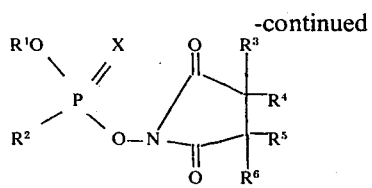

-continued

| No. | X | R¹ | R² | R³ | R⁴ | R⁵ | R⁶ | $n_D^{25}$ or m.p. |
|---|---|---|---|---|---|---|---|---|
| 22 | S | $C_2H_5$ | $C_2H_5O$ | $C_6H_5$ | $C_6H_5$ | H | H | |
| 23 | S | $C_2H_5$ | $C_2H_5O$ | (cyclopentyl) | | H | H | |
| 24 | S | $C_2H_5$ | $C_2H_5O$ | (cyclohexyl) | | H | H | 1.4950 |
| 25 | S | $C_2H_5$ | $C_2H_5O$ | (cyclopentyl) | | $CH_3$ | H | |
| 26 | S | $C_2H_5$ | $C_2H_5O$ | (cyclohexyl) | | $C_2H_5$ | H | |
| 27 | S | $C_2H_5$ | $C_2H_5O$ | (cyclohexyl) | | $nC_3H_7$ | H | |
| 28 | S | $C_2H_5$ | $C_2H_5O$ | $C_2H_5$ | $CH_3$ | H | H | |
| 29 | S | $C_2H_5$ | $C_2H_5O$ | $nC_3H_7$ | $CH_3$ | H | H | |
| 30 | S | $C_2H_5$ | $C_2H_5O$ | $C_2H_5$ | $C_2H_5$ | H | H | |
| 31 | S | $C_2H_5$ | $C_2H_5O$ | $C_2H_5$ | $nC_3H_7$ | H | H | |
| 32 | S | $C_2H_5$ | $C_2H_5O$ | $nC_4H_9$ | $CH_3$ | H | H | |
| 33 | S | $C_2H_5$ | $C_2H_5O$ | $nC_4H_9$ | $nC_4H_9$ | H | H | |
| 34 | S | $C_2H_5$ | $C_2H_5O$ | $nC_5H_9$ | $CH_3$ | H | H | |
| 35 | S | $CH_3$ | $CH_3O$ | $nC_3H_7$ | $CH_3$ | H | H | |
| 36 | S | $CH_3$ | $CH_3O$ | $nC_3H_7$ | $C_2H_5$ | H | H | |
| 37 | S | $CH_3$ | $CH_3O$ | $nC_3H_7$ | $CH_3$ | $CH_3$ | H | |
| 38 | S | $C_2H_5$ | $C_2H_5O$ | =C(CH₃)(CH₃) | | H | H | |
| 39 | S | $C_2H_5$ | $C_2H_5O$ | 2-octen-yl-1 | H | H | H | |
| 40 | S | $CH_3$ | $CH_3O$ | 2-octen-yl-1 | H | H | H | |
| 41 | S | $C_2H_5$ | $C_2H_5O$ | n-octyl-1 | H | H | H | |
| 42 | S | $CH_3$ | $CH_3O$ | n-octyl-1 | H | H | H | |
| 43 | S | $C_2H_5$ | $C_2H_5O$ | n-nonyl-1 | H | H | H | |
| 44 | S | $C_2H_5$ | $C_2H_5O$ | $CH_3$ | H | $CH_3$ | H | |
| 45 | S | $CH_3$ | $CH_3O$ | $CH_3$ | H | $CH_3$ | H | |
| 46 | S | $C_2H_5$ | $C_2H_5O$ | $C_2H_5$ | H | $nC_3H_7$ | H | |
| 47 | S | $CH_3$ | $CH_3O$ | $C_2H_5$ | H | $nC_3H_7$ | H | |

The following compounds were used for the biological experiments:

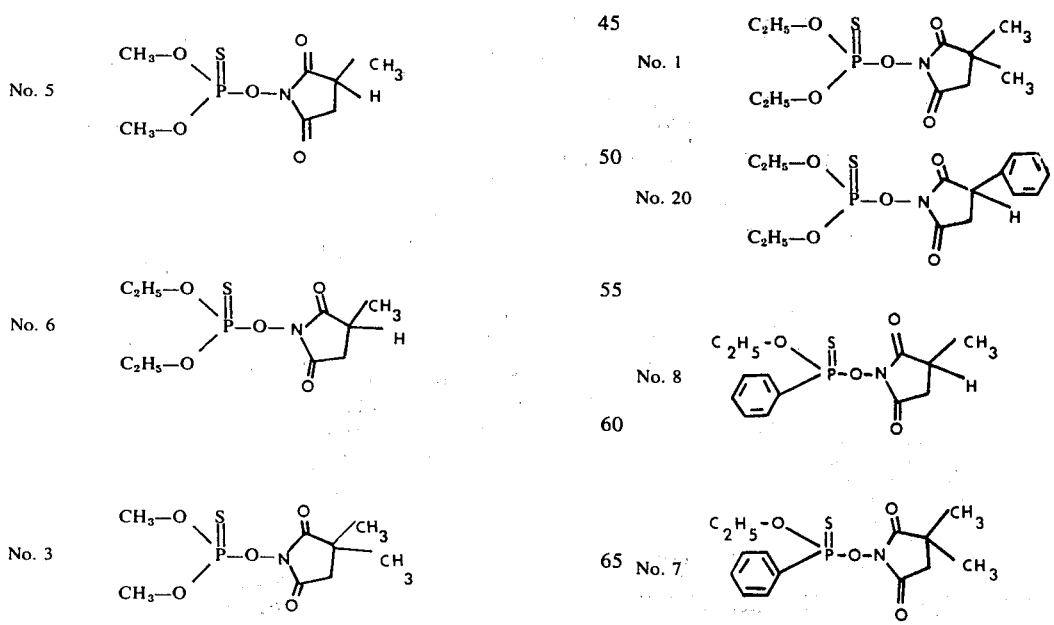

-continued

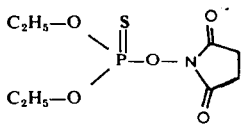

comparative agent (German 962,608)

EXAMPLE 2

Action on caterpillars of the cabbage moth (*Plutella maculipennis*)

Cabbage leaves are dipped in aqueous formulations of the active ingredients. After the layers have dried caterpillars in the 4th stage are placed on the leaves. The mortality is determined after 48 hours.

| Active ingredient | Concentration of the active ingredient (in wt%) | Mortality |
|---|---|---|
| 5 | 0.05 | 95% |
| 6 | 0.02 | 100% |
| 3 | 0.02 | 100% |
| 1 | 0.005 | 90% |
| 8 | 0.01 | 80% |
| 7 | 0.01 | 80% |
| I | 0.1 | 20% |

EXAMPLE 3

Action on bean aphids (*Aphis fabae*)

Potted bean plants harboring heavy aphid colonies were treated in a spray chamber with aqueous dispersions of the active ingredients. The mortality was determined after 24 hours.

| Active ingredient | Concentration of the active ingredient (in wt%) | Mortality |
|---|---|---|
| 5 | 0.01 | 98% |
| 6 | 0.01 | 95% |
| 3 | 0.02 | 100% |
| 1 | 0.005 | 80% |
| 20 | 0.04 | 80% |
| I | 0.1 | 80% |
|   | 0.05 | 30% |

EXAMPLE 4

Action on granary weevils (*Sitophilus granarius*)

The weevils were placed for 4 hours on glass (Petri dishes 10 cm in diameter) treated with the active ingredients. The mortality was determined after 24 hours.

| Active ingredient no. | Amount of active ingredient per dish | Mortality |
|---|---|---|
| 5 | 0.02 mg | 90% |
| 6 | 0.025 mg | 90% |
| 3 | 0.01 mg | 95% |
| 1 | 0.025 mg | 100% |
| I | 1 mg | 35% |

EXAMPLE 5

Culture experiment with *Drosophila larvae* on a nutrient medium treated with active ingredient

| Active ingredient no. | Concentration of active ingredient in medium | Mortality |
|---|---|---|
| 5 | 12.5 ppm | 100% |
| 3 | 5.0 ppm | 100% |
| 1 | 2.5 ppm | 100% |
| 7 | 10.0 ppm | 100% |
| I | 25.0 ppm | 100% |
|   | 12.5 ppm | 50% |

EXAMPLE 6

Contact action on oriental cockroaches (*Blatta orientalis*)

The experiment was carried out in 1 liter beakers the inside surfaces of which had been treated with the active ingredients.

The mortality was determined after 48 hours.

| Active ingredient no. | Amount of active ingredient | Mortality |
|---|---|---|
| 5 | 0.1 mg/beaker | 100% |
| 6 | 0.05 mg/beaker | 100% |
| 3 | 0.1 mg/beaker | 100% |
| 1 | 0.05 mg/beaker | 100% |
| I | 0.25 mg/beaker | 100% |
|   | 0.1 mg/beaker | 40% |

EXAMPLE 7

90 parts by weight of compound 3 is mixed with 10 parts by weight of N-methyl-α-pyrrolidone. A mixture is obtained which is suitable for application in the form of very fine drops.

EXAMPLE 8

20 parts by weight of compound 4 is dissolved in a mixture consisting of 80 parts by weight of xylene, 10 parts by weight of the adduct of 8 to 10 moles of ethylene oxide to 1 mole of oleic acid-N-monoethanolamide, 5 parts by weight of the calcium salt of dodecylbenzenesulfonic acid, and 5 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 9

20 parts by weight of compound 5 is dissolved in a mixture consisting of 40 parts by weight of cyclohexanone, 30 parts by weight of isobutanol, 20 parts by weight of the adduct of 7 moles of ethylene oxide to 1 mole of isooctylphenol, and 10 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 10

20 parts by weight of compound 5 is dissolved in a mixture consisting of 25 parts by weight of cyclohexanol, 65 parts by weight of a mineral oil fraction having a boiling point point between 210° and 280°C, and 10 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 11

20 parts by weight of compound 3 is well mixed with 3 parts by weight of the sodium salt of diisobutylnaphthalene-α-sulfonic acid; 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquid is obtained containing 0.1% by weight of the active ingredient.

EXAMPLE 12

3 parts by weight of compound 4 is intimately mixed with 97 parts by weight of particulate kaolin. A dust is obtained containing 3% by weight of the active ingredient.

EXAMPLE 13

30 parts by weight of compound 6 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

We claim:

1. A succinic acid oximidophosphoric ester of the formula

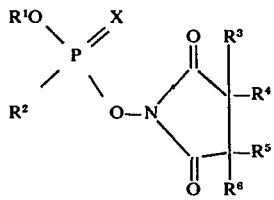

where X is sulfur, $R^1$ is lower alkyl, $R^2$ is lower alkoxy or phenyl, $R^3$ is lower alkyl or phenyl, $R^4$ is hydrogen or lower alkyl, $R^5$ and $R^6$ are hydrogen and $R^3$ and $R^4$ when taken together form a hydrocarbon ring of five or six members.

2. The compound of the formula

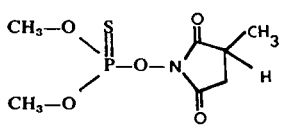

3. The compound of the formula

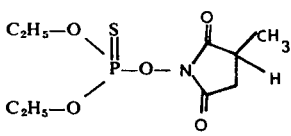

4. The compound of the formula

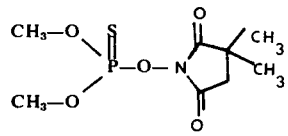

5. The compound of the formula

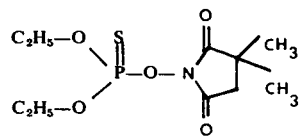

6. The compound of the formula

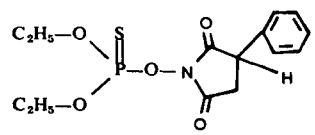

7. The compound of the formula

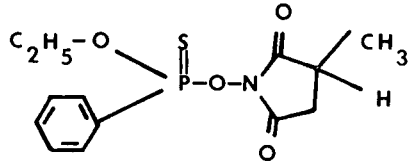

8. The compound of the formula

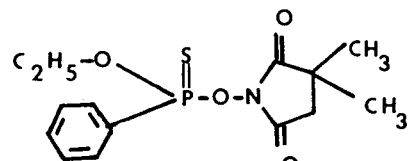

* * * * *